US010605710B2

(12) United States Patent
Carredano et al.

(10) Patent No.: US 10,605,710 B2
(45) Date of Patent: Mar. 31, 2020

(54) METHOD FOR PREPARATION OF LIQUID MIXTURES

(71) Applicant: GE Healthcare Bio-Sciences AB, Uppsala (SE)

(72) Inventors: Enrique Napoleon Carredano, Uppsala (SE); Elenor Strandberg, Sigtuna (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 426 days.

(21) Appl. No.: 15/022,501

(22) PCT Filed: Sep. 26, 2014

(86) PCT No.: PCT/SE2014/051109
§ 371 (c)(1),
(2) Date: Mar. 16, 2016

(87) PCT Pub. No.: WO2015/047173
PCT Pub. Date: Apr. 2, 2015

(65) Prior Publication Data
US 2016/0231207 A1    Aug. 11, 2016

(30) Foreign Application Priority Data

Sep. 30, 2013   (SE) ...................................... 1351142

(51) Int. Cl.
| | |
|---|---|
| *G01N 31/22* | (2006.01) |
| *B01J 47/15* | (2017.01) |
| *G01N 1/38* | (2006.01) |
| *G05D 21/02* | (2006.01) |
| *G01N 27/06* | (2006.01) |
| *G01N 21/33* | (2006.01) |
| *G01N 21/3577* | (2014.01) |
| *G01N 21/41* | (2006.01) |
| *G01N 31/00* | (2006.01) |

(52) U.S. Cl.
CPC ................ *G01N 1/38* (2013.01); *B01J 47/15* (2017.01); *G01N 21/33* (2013.01); *G01N 21/3577* (2013.01); *G01N 21/41* (2013.01); *G01N 27/06* (2013.01); *G05D 21/02* (2013.01)

(58) Field of Classification Search
CPC ........ G01N 31/22; G01N 31/00; G01N 31/80; G01N 31/78; G01N 31/77; G01N 31/75; B01J 47/15; B01J 47/14

USPC ......................................................... 436/163
See application file for complete search history.

(56) References Cited

U.S. PATENT DOCUMENTS

| | | | |
|---|---|---|---|
| 2007/0289925 A1 | 12/2007 | Kawarai et al. | |
| 2010/0219164 A1 | 9/2010 | Kawarai et al. | |
| 2011/0039712 A1 | 2/2011 | Bjorkesten et al. | |
| 2012/0217192 A1* | 8/2012 | Blank ................. | B01D 15/166 |
| | | | 210/143 |

FOREIGN PATENT DOCUMENTS

| | | | |
|---|---|---|---|
| CN | 101675331 A | 3/2010 | |
| CN | 102016567 A | 4/2011 | |
| CN | 103249478 A | 8/2013 | |
| EP | 2269055 B1 | 1/2011 | |
| EP | 3052226 A1 | 8/2016 | |
| JP | 64-21344 A | 1/1989 | |
| JP | 2007268397 A | 10/2007 | |
| WO | WO2009/131524 A1 * | 10/2009 | ............. G01N 30/34 |
| WO | 2011/162666 A1 | 12/2011 | |
| WO | 2012082061 A1 | 6/2012 | |
| WO | 2015/047173 A1 | 4/2015 | |

OTHER PUBLICATIONS

International Preliminary Report on Patentability Received for PCT Application No. PCT/SE2014/051109, dated Apr. 14, 2016, 9 Pages.
Office Action Received for Chinese Patent Application No. 201480053772.X, dated May 9, 2017 (6 Pages of English Translation only).
Extended European Search Report Received for European Patent Application 14848398.5, dated Jul. 31, 2017, 8 Pages.
International Search Report and Written Opinion regarding international application No. PCT/SE2014/051109, dated Dec. 16, 2014, 12 pages.

* cited by examiner

*Primary Examiner* — Christine T Mui
(74) *Attorney, Agent, or Firm* — Eversheds Sutherland (US) LLP

(57) ABSTRACT

The present invention relates to the preparation of liquid mixtures, and more particularly to the preparation of a liquid mixture, such as a buffer, wherein the conductivity of the liquid mixture is measured and the pH indirectly determined if the buffer concentration is known. Another object of the present invention is to provide a method of preparing a liquid mixture with a predetermined pH value by using conductivity as feedback control parameter.

19 Claims, 3 Drawing Sheets

METHOD FOR PREPARATION OF LIQUID MIXTURES

CROSS-REFERENCE TO RELATED APPLICATIONS

This application is a filing under 35 U.S.C. 371 of international application number PCT/SE2014/051109, filed Sep. 26, 2014, which claims priority to Swedish application number SE 1351142-3, filed Sep. 30, 2013, the entire disclosures of each of which are hereby incorporated by reference.

FIELD OF THE INVENTION

The present invention relates to a method for the preparation of liquid mixtures, and more particularly to the preparation of a liquid mixture, such as a buffer, wherein the conductivity of the liquid mixture is measured and the pH indirectly determined.

BACKGROUND OF THE INVENTION

A buffer solution is typically an aqueous solution consisting of a mixture of a weak acid and its conjugate base, or a weak base and its conjugate acid, and has the property that the pH of the solution changes very little when a small amount of strong acid or base is added to it. Buffer solutions are therefore used as a means of keeping pH at a nearly constant value in a wide variety of chemical applications, including e.g. chromatography, filtration, etc. In general, a buffer solution may be made up of more than one weak acid and its conjugate base. For instance, a wider buffer region may be created by mixing two buffering agents with overlapping individual buffer regions.

A buffer solution having a desired pH, and optionally, with a desired ionic strength, may be prepared by calculating the necessary amounts of the ingredients of the buffer and mixing them. While it is often necessary to solve several different equations for calculating the pH of a relatively simple mixture of a weak acid (or base) and a weak base (or acid) depending on their relative concentrations, there is commercial software available for performing such calculations.

Another possibility is to use feedback control as in WO/2011/162666 where the accuracy of the pH measurement limits the accuracy of the pH of the buffer. However calibration of pH meters is both time consuming and often troublesome. The pH meters may not be very accurate, have slow responses and may be easily contaminated by salts for example. The pH measurement is also dependent on temperature, with different buffers having a variety of temperature constants. Usually the reading of the pH meters cannot be corrected to a standard temperature.

Thus, there is still a need within the art to improve pH-measurements and to provide reliable instruments for this purpose.

SUMMARY OF THE INVENTION

The present invention provides a reliable method and means for measurement of pH which avoids the drawbacks of prior art.

The present invention relates to a method to indirectly determine the pH of a buffer solution if its conductivity and concentration are known by using a surface model equation of the form $$pH = f(\text{conductivity}, \text{concentration})$$

or $$pH = f(\text{conductivity}, \text{buffer concentration}, \text{salt concentration})$$

where the surface model equation has been previously obtained by fitting such equation to previously measured pH values for a training data set. The training data set comprises values for the measured or controlled concentration and the measured conductivity of solutions containing the buffer at a plurality of different concentrations and conductivities, and optionally different temperatures, and the surface model equation is obtained by fitting the resulting data to the formula described.

In a first aspect the invention relates to a method of preparing a liquid mixture with a predetermined pH value without using a pH meter by adding and reducing controlled amounts of buffer components, preferably in liquid form, to said liquid mixture; and stop adding and reducing buffer components when a specific conductivity value is obtained, wherein the reduction and addition of buffer components is done in such a way as to maintain the buffer concentration constant and wherein said specific conductivity value corresponds to the predetermined pH value of said liquid, and wherein said specific conductivity value is correlated to said predetermined pH value and the buffer concentration by a mathematical model, such as a surface model equation performed on a specific buffer system.

The invention also relates to a method to indirectly determine the pH of a buffer solution by measuring its conductivity and measuring or controlling the buffer concentration, and wherein said specific conductivity value is correlated to said predetermined pH value by a mathematical model.

When using a surface model equation it may be of the form $$pH = A + B^*\text{concentration} + C^*\text{concentration}^{\wedge}2 + D^*\text{conductivity}$$

wherein A, B and C and D are buffer system specific constants.

Alternatively the surface model equation may be of the form $$pH = A + B^*\text{concentration} + C^*\text{concentration}^{\wedge}2 + D^*\text{conductivity} + E^*\text{conductivity}^{\wedge}2$$

wherein A, B and C and D and E are buffer system specific constants

In an alternative embodiment the surface function giving the predicted pH as function of the conductivity and concentrations is obtained through regression modelling of training set of mixtures with known concentration, conductivity and pH.

The concentration of the buffer may be measured by any of the following IoR, IR, and UV absorbance at several wavelengths.

An alternative way of measuring or controlling the buffer concentration is to prepare stock solutions of acid and base respectively to a known concentration for instance by diluting weighted amounts of buffer salts to measured volumes and then to control or measure the flow from the stock solutions and of water to the common point of mixture of the buffer. Yet another way to control or measure the buffer concentration is to measure the conductivity or another property like IR light absorbance or other absorbance or the IoR signal on the stock solutions, then use those signals to back calculate the concentration of the stock solutions using beforehand determined conductivity (or IR or IoR) versus concentration curves. Using the information obtained in this way on the concentration of the stock solutions and the information on the measured or controlled flows to the mixing point it is then possible to calculate the concentration of the mixed buffer.

With the knowledge of the buffer concentration and the conductivity of the buffer it is possible according to the present invention to determine the pH using a surface model equation of the pH as function of the conductivity and the concentration of the buffer solution. For every type of buffer solution such a surface model equation can be pre-determined by (i) using a training data set belonging to the relevant area of concentration and conductivity considered. (ii) Measuring the pH for the solutions belonging to the training data set and (iii) using a numerical regression method like for instance multi-linear regression (MLR) or partial least squares (PLS) method to obtain the surface model equation as a regression model from the data.

Preferably the method according to the invention is computer-implemented.

In a second aspect, the invention relates to use of the above described method for controlling a buffer formulation system or an in-line dilution system. The method may also be used in screening experiments wherein pH and concentration is used as a design of experiment (DoE) parameter.

In a third aspect, the invention relates to a device comprising a computer program product comprising instructions for causing a computer to perform the method as described above.

The device may comprise a conductivity sensor and concentration sensor and means for calculating pH from measured conductivity using the above described method.

The device may also allow input of buffer concentration and include means for calculating pH from measured conductivity using the steps of the above described method.

In the following, the invention will be described in more detail, by way of example only, reference being made to the accompanying drawing.

Figure 1:
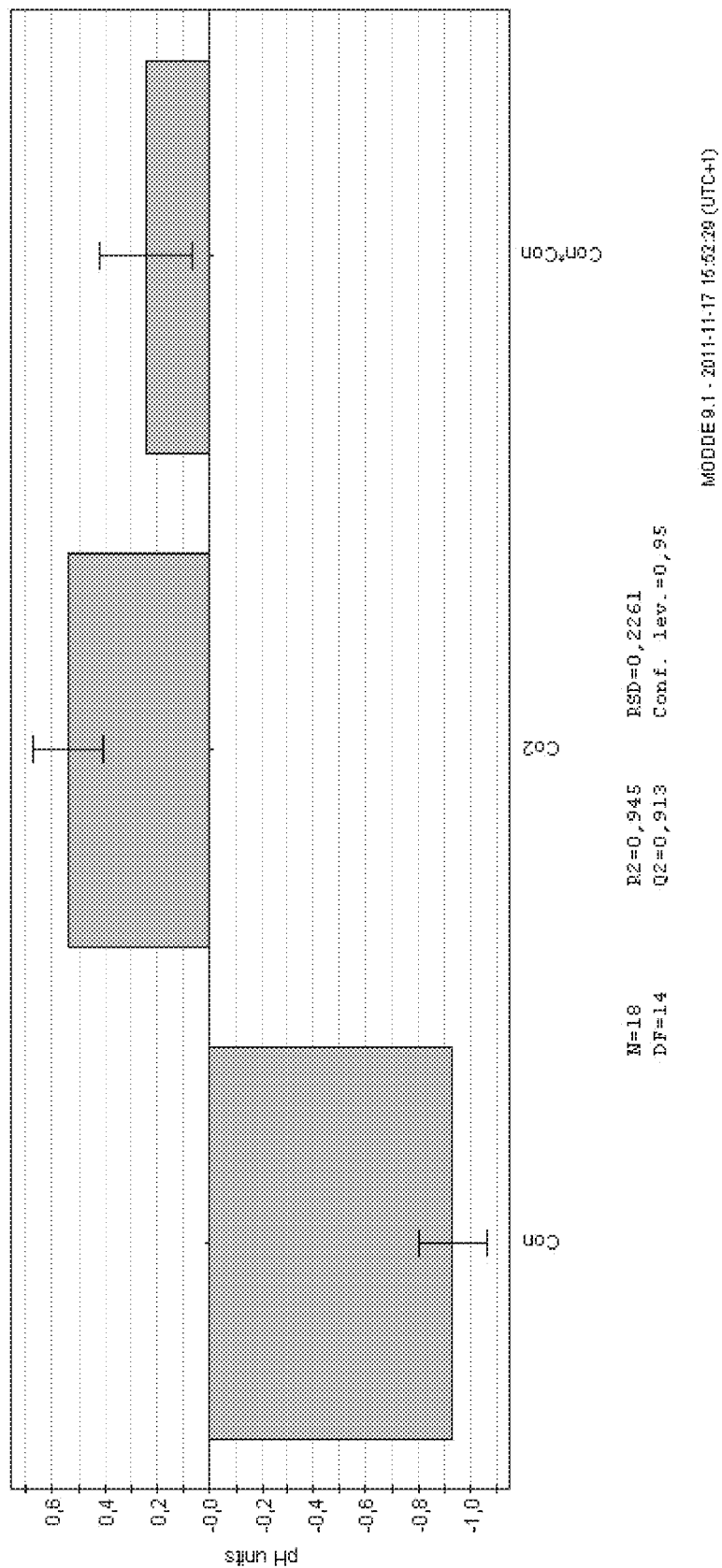
FIG. 1 shows the results from scaled and centred coefficients for pH according to the experimental details in Example 1 below.

In order to facilitate an understanding of the disclosed invention, a number of terms will be defined below.

Definitions

Buffer

As used herein, a buffer solution is an aqueous solution typically consisting of a mixture of a weak acid and its conjugate base or a weak base and its conjugate acid. It has the property that the pH of the solution changes very little when a small amount of strong acid or base is added to it. Buffer solutions are used as a means of keeping pH at a nearly constant value in a wide variety of chemical applications Conductivity (Electrolytic)

The conductivity (or specific conductance) of an electrolyte solution is a measure of its ability to conduct electricity. The SI unit of conductivity is "siemens" per meter (S/m).

Ionic Strength

The ionic strength of a solution is a function of the concentration of all ions in the solution (half the sum of concentration multiplied by the square of ionic charge for all ions). The ionic strength is typically given in the unit $mol/dm^3$.

Surface Model Equation

A surface model equation as used here is a function of the form $f(x,y)$ where x and y are two independent variables which are properties of a buffer solution. More specifically in this context x (or y) refers to the conductivity of the buffer solution and y (or x) refers to the buffer concentration.

DETAILED DESCRIPTION OF THE INVENTION

As mentioned above, the present invention relates to the preparation of liquid mixtures, and more particularly to the preparation of a liquid mixture, such as a buffer, wherein the conductivity of the liquid mixture is measured and the pH indirectly determined if the buffer concentration is known. Furthermore the invention relates to the provision of a method of preparing a liquid mixture with a predetermined pH value by using conductivity as feedback control parameter. Below the methods used for predicting pH, determination of surface model equation and calculation of pH are described, respectively.

Predicting the pH

One object of the present invention is thus is indirectly determine the pH of a buffer solution if its conductivity and concentration are known. As compared to pH measurements, conductivity measurements are fast and reliable and can be temperature corrected to for instance room temperature 25 degrees C. as standard. Furthermore, usually calibration on a yearly basis is enough for conductivity meters. Thus it should be advantageous to measure the conductivity instead of the pH.

The present invention provides also a method of preparing a buffer with a given buffer concentration to a predetermined pH value without using a pH meter. There are other methods where this is possible to do for instance a buffer solution with a desired pH, and optionally, with a desired ionic strength, may be accurately prepared by calculating the necessary amounts of buffer ingredients and mixing them as previously described in EP 2269055 B1. However in contrast to those methods, the method described in the present invention does not use recipes and instead uses measured conductivity as feedback control parameter. The use of feedback control to obtain a buffer with desired properties is not new. For instance one such method is described in WO/2011/162666. Nevertheless, there is a large difference and advantage as compared to that method where measured pH is necessary as control parameter. In the present case, the correct buffer with correct pH and buffer concentration is obtained by combining conductivity measurement with control of buffer concentration by some means.

The measuring or controlling of the buffer concentration may be achieved in different ways. For instance the measuring or controlling of the buffer concentration may be achieved by using Index of Refraction (IoR) techniques or Infra Red (IR) spectroscopy, UV absorbance or other methods.

An alternative way of measuring or controlling the buffer concentration is to prepare stock solutions of acid and base respectively to a known concentration for instance by diluting weighted amounts of buffer salts to measured volumes and then to control or measure the flow from the stock solutions and of water to the common point of mixture of the buffer. Yet another way to control or measure the buffer concentration is to measure the conductivity or another property like IR light absorbance or other absorbance or the IoR signal on the stock solutions, then use those signals to back calculate the concentration of the stock solutions using beforehand determined conductivity (or IR or IoR) versus concentration curves. Using the information obtained in this way on the concentration of the stock solutions and the information on the measured or controlled flows to the mixing point it is then possible to calculate and control the concentration of the mixed buffer.

Thus as it is possible according to this invention to calculate the pH by monitoring the conductivity of the buffer as long as the buffer concentration is calculated or controlled it is also possible to determine the amount of ingredients, acid and base with conductivity feedback control.

Whether the method described in here is used for predicting the pH of a buffer or for using conductivity feedback control to produce a buffer with correct pH and buffer concentration a central feature of this invention is the determination of a surface model equation for the pH as function of the conductivity and the buffer concentration in other words a function of the form f(x,y) where x (or y) refers to the conductivity of the buffer solution and y (or x) refers to the buffer concentration. It will be now described how this equation can be obtained.

Determination of Surface Model Equation

The surface model equation of the form pH=$f$(conductivity,concentration)

or pH=$f$(conductivity, buffer concentration, salt concentration)

for the buffer can be produced by fitting obtained pH data from a finite number of points in the (conductivity, concentration) space to the equation above. Design of Experiments (DoE) can be used with advantage but is not necessary. This step is not difficult to do for anyone skilled in the art of fitting an equation to the data measured for a training set. The obtained equation is valid within certain accuracy in the area covered by the discrete number of points in the training set.

Calculation of pH

Finally, the pH is calculated as predicted pH of the desired buffer solution by using the above described surface model equation and measured values of conductivity together with corresponding measured or controlled values of the buffer concentration.

The method of the invention may be implemented by software run on an electrical data processing device, such as a computer. Such software may be provided to the computer on any suitable computer-readable medium, including a record medium, a read-only memory, or an electrical or optical signal which may be conveyed via electrical or optical cable or by radio or other means.

Predicting the pH as described above has not been described before somewhere else. In previous occasions, the prediction of the pH or the formulations of buffers at a given pH have been described. For instance in US20110039712 A1 and EP 2269055 B1, but those methods or similar methods do not use conductivity and require recipes. On the other hand, another method describes the prediction of conductivity from it's constituents PCT SE2011/051513 but that method does not describe how the pH could be retrieved from conductivity measurement without needing to calculate for each ionic species of said plurality of species the molar conductivity by the formula:

$$\Lambda = \Lambda_0 - K \times \text{Sqrt}(c)$$

wherein $\Lambda$ is the molar conductivity, $\Lambda_0$ is the molar conductivity at infinite dilution, c is the concentration of the ionic species, and K is the Kohlrausch coefficient, and wherein K and $\Lambda_0$ are obtained from a data set comprising predetermined values for K and $\Lambda_0$ for each ionic species.

Predicting the pH as described here requires only the calibration of a surface equation of the form pH=$f$(conductivity, buffer concentration)

or pH=$f$(conductivity, buffer concentration, salt concentration)

with a valid range at a given accuracy and simply the measurement of the conductivity and the control or measurement of the buffer concentration and if necessary the salt concentration. Predicting the pH as described here does not require to calculate for each ionic species the molar conductivity, or $\Lambda_0$ is the molar conductivity at infinite dilution or Kohlrausch coefficients.

Predicting the pH as described here may be used for several purposes. Exemplary applications include the use for controlling a buffer formulation system or an in-line dilution system. Such prediction of pH may also be used in screening experiments wherein pH and concentration (but not conductivity) are used as design of experiment (DoE) parameters. Still another application is for determining the exact concentration of a stock solution or a buffer by measuring its pH and conductivity.

The method described above may be used to obtain the specific surface model for a specific buffer system in conjunction with a specific concentration of non-buffer salt (for instance NaCl). One can also generalize the surface equation to include concentration of salt, i.e. f(x,y,z) where z is concentration of salt. Alternatively keep the concentration of NaCl constant and obtain one model for each concentration of NaCl.

The invention will now be described in more detail, by way of example only, by the following non-limiting Examples.

EXAMPLES

Example 1: Surface Model Equation for the pH as Function of the Concentration and the Conductivity In this experiment, the conductivity and the buffer concentration has been used to indirectly determine the pH. Modde version 9.0 was used to obtain the surface model equation as a regression model including the coefficients of the model. Three different concentration levels and six different conductivity values for each concentration of citrate buffer were included in the training set (table). The buffers were mixed using a lab scale Äkta explorer system (GE Healthcare Biosciences AB) with five pumps with Unicorn 5 control software (GE Healthcare Biosciences AB) where the concentration was controlled by setting the flow manually from stock solutions of acid (0.5 M citric acid) and base (0.5 M Na3 citrate) and from water. The conductivity was measured off-line using linear temperature correction with constant 2.1 and the pH was measured off-line using a calibrated HANNA pH meter.

TABLE 1

| No | Concentration (mM) | Conductivity (mS/cm) | pH (measured off-line) |
|---|---|---|---|
| 1 | 20 | 1.511 | 3.89 |
| 2 | 20 | 1.997 | 4.34 |
| 3 | 20 | 2.51 | 4.73 |
| 4 | 20 | 3.01 | 5.15 |
| 5 | 20 | 3.49 | 5.58 |
| 6 | 20 | 4.01 | 6.06 |
| 7 | 50 | 2.51 | 3.33 |
| 8 | 50 | 2.99 | 3.6 |
| 9 | 50 | 3.47 | 3.83 |
| 10 | 50 | 3.97 | 4.04 |
| 11 | 50 | 4.47 | 4.23 |
| 12 | 50 | 4.95 | 4.4 |
| 13 | 80 | 2.48 | 2.81 |
| 14 | 80 | 2.97 | 3.03 |
| 15 | 80 | 3.49 | 3.22 |
| 16 | 80 | 3.97 | 3.39 |
| 17 | 80 | 4.45 | 3.57 |
| 18 | 80 | 4.99 | 3.72 |

Partial least square regression analysis was used to obtain a surface model equation as a relationship among concentration, conductivity and pH (FIG. 1).

A test set with seven citrate buffers was done to test the prediction capability of the model (table).

TABLE 2

Test set for prediction capability test of the model.

| Concentration (mM) | Conductivity (mS/cm) | pH (measured off-line) | Predicted pH | Lower value | Upper value |
|---|---|---|---|---|---|
| 30 | 3.95 | 4.92 | 5.01 | 4.82 | 5.20 |
| 30 | 2.45 | 4.08 | 4.20 | 4.01 | 4.38 |
| 40 | 2.48 | 3.63 | 3.73 | 3.50 | 3.96 |
| 40 | 4.45 | 4.59 | 4.80 | 4.58 | 5.02 |
| 70 | 2.96 | 3.18 | 3.00 | 2.80 | 3.19 |
| 70 | 3.97 | 3.57 | 3.54 | 3.39 | 3.70 |
| 70 | 4.95 | 3.91 | 4.08 | 3.86 | 4.29 |

Figure 2:
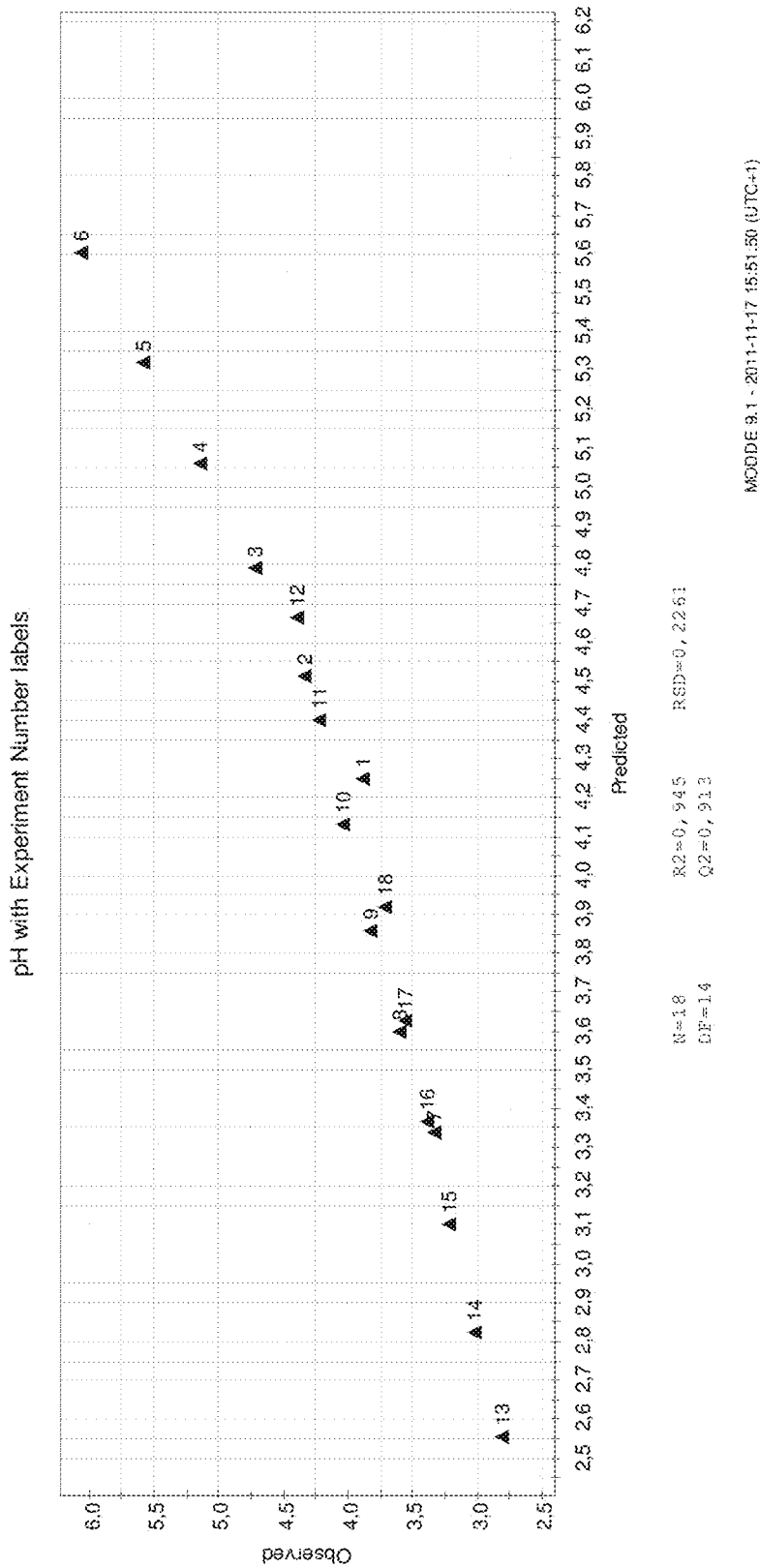
FIG. 2 shows a graph of the observed versus predicted values of pH according to the experimental details in Example 1 below.

The measured pH values for all of the runs were in the predicted interval so that the model has been proved to be capable of allowing indirect determination of the pH (FIG. 2).

Example 2: Making a Buffer of a Given pH Using Conductivity Feedback Control

Figure 3:
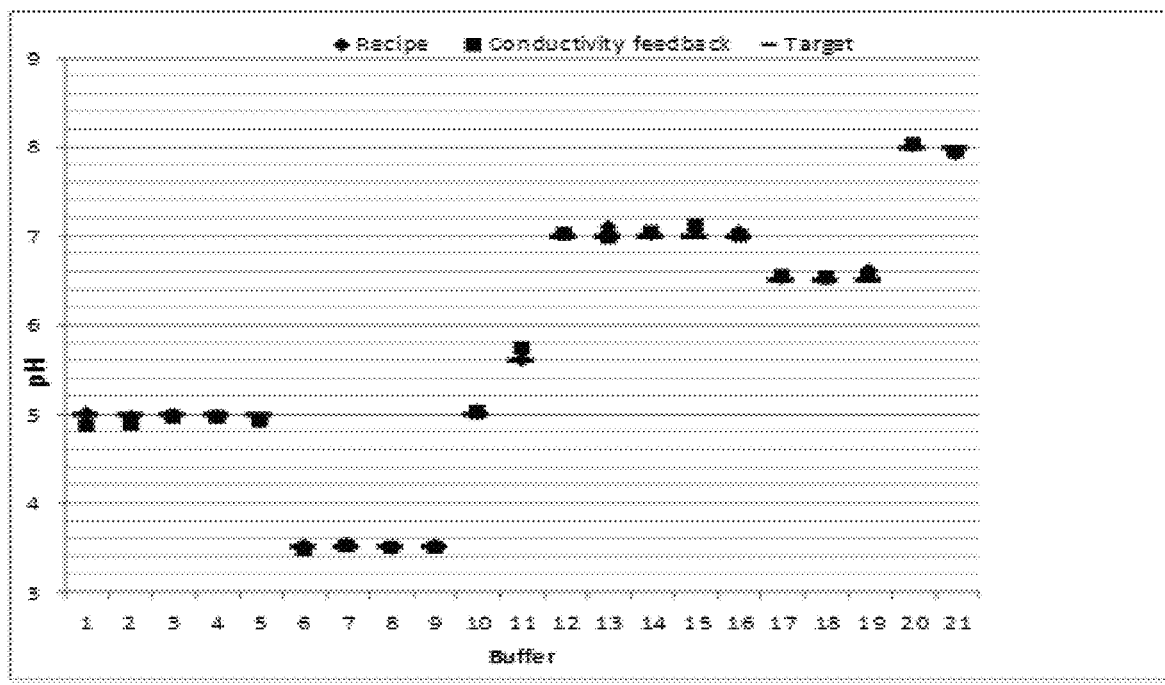
FIG. 3 shows a graph showing the resulting measured pH values from buffers prepared in two different ways. By recipes and by "pH by conductivity-feedback". Both values are compared to target value, see Example 2 below.

It is an object of the present invention to provide a method of preparing a liquid mixture with a predetermined pH value by using conductivity as feedback control parameter. No recipes and no in-line pH meters are necessary in this case. A total of 21 different buffers were used to compare buffer preparation in this way (Table 3) and compared to a second case where the flows of the incoming solutions were controlled and the buffers were prepared using recipes. The target conductivity values for the first method which is the method described in the present invention were the conductivity values obtained by measuring the temperature corrected conductivity from the result files of the second method. According to the results, preparation of buffers through conductivity feedback showed no difference in pH compared to buffers prepared by recipes and pH meters (FIG. 3).

TABLE 3

Buffers prepared in two different ways, by recipes and by conductivity feedback.

| 1 | Buffer system | Stock solution 1 | Stock solution 2 | Stock solution 3 |
|---|---|---|---|---|
| 1 | 20 mM acetate pH 5.0 | 0.5M | 1.0M | n/a |
| 2 | 20 mM acetate pH 5.0 1M NaCl | HAc | NAc*3H20 | 3M NaCl |
| 3 | 100 mM acetate pH 5.0 | | | n/a |
| 4 | 100 mM acetate pH 5.0 1M NaCl | | | 3M NaCl |
| 5 | 100 mM acetate pH 5.0 2M NaCl | | | 3M NaCl |
| 6 | 20 mM citrate pH 3.5 | 0.5M | 0.5M | n/a |
| 7 | 20 mM citrate pH 3.5 1M NaCl | Citric acid * | Na3 Citrate | 3M NaCl |
| 8 | 100 mM citrate pH 3.5 | 1H20 | *2H2O | n/a |
| 9 | 100 mM citrate pH 3.5 1M NaCl | | | 3M NaCl |
| 10 | 25 mM citrate pH 5.0 200 mM NaCl | | | 1M NaCl |
| 11 | 25 mM citrate pH 5.6 225 mM NaCl | | | 1M NaCl |
| 12 | 20 mM phosphate pH 7 | 0.4M | 0.4M | n/a |
| 13 | 20 mM phosphate pH 7 1M NaCl | NaH2PO4 * | Na2HPO4* | 3M NaCl |
| 14 | 50 mM phosphate pH 7 | 1H2O | 2H2O | n/a |
| 15 | 50 mM phosphate pH 7 1M NaCl | | | 3M NaCl |
| 16 | 50 mM phosphate pH 7 2M NaCl | | | 3M NaCl |
| 17 | 30 mM phosphate pH 6.5 | | | n/a |
| 18 | 30 mM phosphate pH 6.5 50 mM NaCl | | | 1M NaCl |
| 19 | 30 mM phosphate pH 6.5 1M NaCl | | | 3M NaCl |
| 20 | 20 mM Tris pH 8 | 0.3M | 0.3M | n/a |
| 21 | 50 mM Tris pH 8 1M NaCl | Tris base | Tris HCl | 3M NaCl |

The invention claimed is:

1. A method of preparing a buffer system having a predetermined pH value without using a pH meter, the method comprising,
   measuring the conductivity of the buffer system using a conductivity sensor;
   measuring or calculating the concentration of the buffer system;
   adding and reducing controlled amounts of buffer components to said buffer system based on the measured conductivity and the measured or calculated concentration of the buffer system to maintain buffer concentration constant; and
   stop adding and reducing buffer components when a specific conductivity value is obtained,
   wherein said specific conductivity value is correlated to said predetermined pH value and the buffer concentration by a surface model equation and the method further comprising
   using a training data set with known concentrations, specific conductivities and pHes obtained from a training set of solutions; and
   measuring the pH for the solutions belonging to the training data set and using a numerical regression method to obtain the surface model equation as a regression model from the training data.

2. The method of claim 1, wherein the buffer system is an acetate buffer system, a citrate buffer system, a phosphate buffer system, or a Tris buffer system.

3. The method of claim 1, wherein the surface model equation is of the form:
   pH=A+B*concentration of the buffer system+C*concentration of the buffer system $^2$+D* specific conductivity; and
   wherein A, B, C, and D are buffer system specific constants determined through the regression modelling of the training data.

4. The method of claim 1, wherein the surface model equation is of the form;
   pH=A+B*concentration of the buffer system+C*concentration of the buffer system $^2$+D* specific conductivity+E* specific conductivity $^2$; and
   wherein A, B, C, D, and E are buffer system specific constants determined through the regression modelling of the training data.

5. The method of claim 1, wherein the concentration of the buffer system is measured by any of Index of Refraction (IoR), Infrared Red (IR), and Ultraviolet (UV) absorbance at several wavelengths.

6. The method of claim 1, wherein the concentration of the buffer system is calculated from the known flows from stock solutions of known concentrations and the flows of other components like water and non-buffering salts or additives to the point of mixture of the buffer.

7. The method of claim 1, wherein the concentration of the buffer system is calculated from the measured conductivities, IR values, or IoR values and known flows from stock solutions and the flows of other components like water and non-buffering salts or additives to the point of mixture of the buffer.

8. The method of claim 1, which is computer-implemented.

9. A method for controlling a buffer formulation system, the method comprising using the method of claim 1.

10. A method for controlling an in-line dilution system, the method comprising using the method of claim 1.

11. A method for screening experiments wherein pH and the concentration of the buffer system is used as a design of experiment (DoE) parameter, the method comprising using the method of claim 1.

12. A device comprising a computer and a computer program product comprising instructions for causing the computer to perform a method of preparing a buffer system having a predetermined pH value without using a pH meter, the method comprising,
   measuring the conductivity of the buffer system using a conductivity sensor;
   measuring or calculating the concentration of the buffer system;
   adding and reducing controlled amounts of buffer components to said buffer system based on the measured conductivity and the measured or calculated concentration of the buffer system to maintain buffer concentration constant; and
   stop adding and reducing buffer components when a specific conductivity value is obtained,
   wherein said specific conductivity value is correlated to said predetermined pH value and the buffer concentration by a mathematical model and the method further comprising
   using a training data set with known concentrations, specific conductivities and pHes obtained from a training set of solutions; and
   measuring the pH for the solutions belonging to the training data set and using a numerical regression method obtain a mathematical model as a regression model from the training data.

13. The device of claim 12, further comprising a conductivity sensor and a concentration sensor and the computer for calculating pH from measured conductivity.

14. The device of claim 12, comprising a conductivity sensor and allowing input of buffer concentration and the computer for calculating pH from measured conductivity.

15. A computer implemented method of preparing a buffer system having a predetermined pH value without using a pH meter, wherein the buffer system is an acetate buffer system, a citrate buffer system, a phosphate buffer system, or a Tris buffer system, the method comprising,
   measuring the conductivity of the buffer system using a conductivity sensor;
   measuring or calculating the concentration of the buffer system;
   adding and reducing controlled amounts of buffer components to said buffer system based on the measured conductivity and the measured or calculated concentration of the buffer system to maintain buffer concentration constant; and
   stop adding and reducing buffer components when a specific conductivity value is obtained,
   wherein said specific conductivity value is correlated to said predetermined pH value and the buffer concentration by a surface model equation of the form:
   pH=A+B*concentration of the buffer system+C*concentration of the buffer system $^2$+D* specific conductivity; and
   or
   pH=A+B*concentration of the buffer system+C*concentration of the buffer system $^2$+D* specific conductivity+E* specific conductivity $^2$; and
   wherein A, B, C, D, and E are buffer system specific constants and the method further comprising determining A, B, C, D, and E through using a training data set with known concentrations, specific conductivities and pHes obtained from a training set of solutions; and measuring the pH for the solutions belonging to the training data set and using a numerical regression method to obtain the surface model equation as a regression model from the training data.

16. The method of claim 15, wherein the concentration of the buffer system is measured by any of Index of Refraction (IoR), Infrared Red (IR), and Ultraviolet (UV) absorbance at several wavelengths.

17. The method of claim 15, wherein the concentration of the buffer system is calculated from the known flows from stock solutions of known concentrations and the flows of other components like water and non-buffering salts or additives to the point of mixture of the buffer.

18. The method of claim 15, wherein the concentration of the buffer system is calculated from the measured conductivities, IR values, or IoR values and known flows from stock solutions and the flows of other components like water and non-buffering salts or additives to the point of mixture of the buffer.

19. A device comprising
  a computer program product comprising instructions for causing the computer to perform the method steps of claim 15, and
  a conductivity sensor and concentration sensor and the computer for calculating pH from measured conductivity according to the method of claim 15 or,
  a conductivity sensor and allowing input of buffer concentration and the computer for calculating pH from measured conductivity according to the method of claim 15.

* * * * *